United States Patent [19]

Fournier et al.

[11] Patent Number: 5,387,237
[45] Date of Patent: Feb. 7, 1995

[54] BIOARTIFICIAL PANCREAS

[75] Inventors: Ronald L. Fournier, Sylvania; Peter J. Goldblatt, Toledo; James M. Horner, Sylvania; Jeffrey G. Sarver, Rossford, all of Ohio

[73] Assignee: The University of Toledo, Toledo, Ohio

[21] Appl. No.: 94,946

[22] Filed: Jul. 21, 1993

Related U.S. Application Data

[63] Continuation-in-part of Ser. No. 922,562, Jul. 30, 1992, abandoned.

[51] Int. Cl.$^6$ .......................... A61F 2/02; A61F 2/00; A61M 37/00; A61M 5/32
[52] U.S. Cl. .......................... 623/11; 604/4; 604/175; 424/424; 210/321.6
[58] Field of Search .................. 604/4, 175; 623/11, 623/12; 424/424; 435/283, 284; 210/321.6, 321.87, 321.9

[56] References Cited

U.S. PATENT DOCUMENTS

| | | |
|---|---|---|
| 4,699,141 | 10/1987 | Lamberton et al. ............... 606/135 |
| 5,002,661 | 3/1991 | Chick et al. ............... 604/4 X |
| 5,100,392 | 3/1992 | Orth et al. ............... 128/899 X |
| 5,116,493 | 5/1992 | Chick et al. ............... 604/4 X |
| 5,116,494 | 5/1992 | Chick et al. ............... 604/4 X |

Primary Examiner—Randall L. Green
Assistant Examiner—Elizabeth M. Burke
Attorney, Agent, or Firm—Marshall & Melhorn

[57] ABSTRACT

An implantable bioartificial pancreas device having an islet chamber containing glucose responsive and insulin-secreting islets of Langerhans or similar hormone secreting cells, the islet chamber having baffle means inside thereof to assist in even distribution of the islets in the chamber, one or more vascularizing chambers open to surrounding tissue, a semi-permeable membrane between the islet and vascularizing chambers that allows passage of small molecules including insulin, oxygen and glucose and does not allow passage of agents of the immune system such as white cells and antibodies, the vascularizing chambers containing a growth factor soaked fibrous or foam matrix having a porosity of about 40 to 95%, the matrix providing small capillary growth and preventing the blood from clotting in the lower chamber.

9 Claims, 2 Drawing Sheets

BIOARTIFICIAL PANCREAS

This application is a continuation-in-part application of Ser. No. 07/922,562 filed Jul. 30, 1992 now abandoned.

FIELD OF THE INVENTION

The present invention is directed to a bioartificial implantable pancreas for the treatment of insulin dependent diabetes mellitus.

BACKGROUND OF THE INVENTION

There is a need to provide a biocompatible and implantable device containing islets of Langerhans, or the beta cells thereof, that can supply the hormone insulin for the purpose of controlling blood glucose levels in people with diabetes mellitus requiring insulin. Insufficient regulation of blood glucose levels in people with diabetes has been associated with the development of long-term health problems such as kidney disease, blindness, coronary artery disease, stroke, and gangrene resulting in amputation. Therefore, there is a need to replace conventional insulin injections with a device that can provide more precise control of blood glucose levels. An implantable bioartificial pancreas device which was evaluated in dogs by Monaco et al. was recently described in the following articles: "Successful treatment of diabetes with the biohybrid artificial pancreas in dogs" *Transplantation* 51, 43–51, January, 1991; "Biohybrid artificial pancreas: Long-term implantation studies in diabetic, pancreatectomized dogs" Science 252, 718–721, May 1991; "Transplantation of islet allografts and xenografts in totally pancreatectomized diabetic dogs using the hybrid artificial pancreas" Ann. Surg. 214 339–362 September, 1991. The device described in these articles was a chamber containing a coiled copolymer tubular membrane through which and within which blood flowed. The coiled copolymer tubular membrane had a nominal porosity of 80,000 daltons which permit free passage of nutrients and insulin but inhibit passage of the agents of the immune system (immunoisolation). Surrounding the outside of the coiled tubular membrane and within the chamber were placed islets of Langerhans. The islets of Langerhans are composed primarily of $\alpha$, $\beta$, $\delta$ and PP cells which synthesize and secrete the hormones glucagon, insulin, somatostatin, and pancreatic polypeptide respectively. These cells may interact in unknown ways to regulate the level of serum glucose. The islets are not in direct contact with the blood. Blood flow through the coiled tube was achieved by connecting the ends of the coiled tube to standard vascular grafts which were then anastomosed to blood vessels. In this type of device blood physically contacts and flows through the artificial coiled copolymer tubular membrane which comprises the device. The major limitation of this approach is the formation of blood clots. There is therefore a need for a device which can provide the islets with a non-clotting blood supply which also provides for rapid transfer of essential nutrients as well as glucose and insulin.

U.S. Pat. No. 4,699,141 (Rhode Island Hospital) discloses a neovascularization approach for transplanting cells by placing a ligated blood vessel in a sponge made of a material that is preferably an acrylic copolymer carrying collageno This patent is similar to a concept for an "organoid" described later by two Thompson et al. articles, "Site-directed neovessel formation in vivo" Science, 1349–1352 September, 1988 and "Heparin binding growth factor 1 induces the formation of organoid neovascular structures in vivo" Proc. Nat'l Academy of Science, USA, 86, 7928–7932, 1989. In these articles blood vessel growth was promoted in vivo within a porous matrix consisting of a Gore-tex TM brand of polytetrafluoroethylene (PTFE) fibers containing absorbed growth factor. It was shown that the vascularized PTFE material served as a vehicle for the transplantation of hepatocytes in rats. However, the matrix was not used as a bioartificial pancreas and it provided no protection from the recipient's immune system.

U.S. Pat. No. 5,100,392 describes an implantable device for delivering drugs or other liquid solutions through incorporation of the device into the surrounding tissue. One of the features appears to be the use of a hollow tubular casing of a synthetic porous material that promotes growth of connective tissue. Inlet (and outlet) catheters are used to administer the fluid (including islets) directly to and from the vascularized connective tissues.

The alternative embodiment in this patent (U.S. Pat. No. 5,100,392) for transplanting cells, such as islets of Langerhans, consisting of a plurality of hollow synthetic tubules arranged as a central cylindrical core within the outer casing will result in vascularization of the casing only leaving the tubules containing transplanted cells, such as the islets of Langerhans, either not vascularized or poorly vascularized. Although this poses no real problem for the delivery of drugs or other liquid solutions, in the case of transplanted cells, such as islets, placed within the lumens of the plurality of hollow tubules, this inner core region not being sufficiently vascularized will quickly result in injury and death of the transplanted cells or at best result, for the case of islets as the transplanted cells, in a poor glucose-insulin response with a minimal effect on the level of glucose control in a patient with diabetes mellitus. In the invention presented herein for a bioartificial pancreas, the device geometry is a thin cylindrical disk which results in precise control of the penetration depth of the ingrowing tissue and capillary bed resulting in the transplanted cells, such as the islets of Langerhans, being all at the same uniform distance from the vascularized region of the device. This will result in a more compact and easily implantable device with improved mass transfer characteristics between the transplanted cells and the vascularized region of the device. In the case of a patient with diabetes, the blood glucose control will therefore be normalized.

OBJECTS OF THE INVENTION

It is an object of the present invention to provide an easily implantable, easily used bioartificial pancreas device which provides a site-specific natural, nonclotting blood supply to immunoprotected islets of Langerhans and minimizes fibrotic overgrowth and encapsulation.

It is another object of the invention to provide the above described device with an upper chamber containing the islets of Langerhans (islet chamber) or other secreting cells such as neurons, pituitary, parathyroid, liver, adrenal and ovarian and a means for adding and removing them via an inlet and outlet catheter with ports, and a lower chamber (vascularizing chamber) containing a fibrous or sponge-like matrix having a porosity of about 40 to 90 percent, the matrix having an angiogenic stimulating growth factor such as heparin binding growth factor, collagen, endothethial cell growth factor, acidic and basic fibroblast growth factor material and porous openings with average pore size in the range of 10 to 200 microns to facilitate the growth of the neovessels. The matrix material containing the growth factor stimulates the surrounding tissue of the host to penetrate the matrix and vascularize it much like the process of wound healing, with the result that the device develops its own blood supply after a sufficient period of time, usually within four weeks. The device includes a semipermeable membrane made of any natural or synthetic material providing a molecular weight cut-off of less than 100,000 that is placed between the upper (islet) and lower (vascularizing) chambers to protect the islets of Langerhans from the agents of the host's immune system (immunoisolation) while allowing passage of smaller nutrient molecules such as glucose and oxygen as well as insulin. An extension of this description would include placement of the islets of Langerhans in a central islet chamber which, in one embodiment, is sandwiched between two outer vascularizing chambers containing the growth factor and matrix material, with a means of adding or removing the islets. Semipermeable membranes for immunoprotection of the islets would separate the islets in the central chamber from the outer chambers. Each outer chamber containing the growth factor and matrix would have the same characteristics and functions described above.

It is an object of the present invention to provide a method of using the above bioartificial pancreas device, the method including:

a) providing the bioartificial pancreas as above described in the preceding objects;
b) making the thickness of the pancreas about 1 to 10 millimeters, its diameter depending on the size, weight, and age of the patient as well as the number of islets needed for effective treatment;
c) implanting the pancreas in a mammal; and
d) immunoisolating the implanted islets of Langerhans.

The method also includes:

e) using islet of Langerhans or the beta cells therefrom obtained from a human pancreas or animal sources such as the pig, cow, dog, or rat or insulin secreting cells either naturally occurring or experimentally derived; and
f) a porous support matrix using angiogenic growth factors to stimulate device vascularization which minimizes fibrotic overgrowth and encapsulation.

DESCRIPTION OF THE DRAWINGS

These and other objects will be apparent from the specification that follows, the appended claims, and the drawings in which:

SUMMARY OF THE INVENTION

The present invention provides an implantable bioartificial pancreas comprising a device having an enclosed islet chamber and one or more vascularizing chambers having an opening at one end thereof that provides access to surrounding tissue, a plurality of insulin-secreting islets of Langerhans in the islet chamber, inlet means for supplying islets to the islet chamber, outlet means for removing islets from the islet chamber, a semi-permeable membrane(s) between the islet and vascularizing chambers, the membrane(s) providing a molecular weight cut-off less than about 100,000 thereby immunoprotecting the islets from the vascular area within the vascularizing chamber and around the implanted vascularizing chamber, the membrane(s) allowing passage of molecules with molecular weights less than 100,000, including glucose, oxygen and insulin between the islet and vascularizing chambers and not allowing passage of agents of the immune system such as leukocytes, antibodies, and complement to the islet chamber, and a biocompatible fibrous or porous foam matrix in the vascularizing chamber to provide a neovascular formation region for enhancing the growth of small capillaries for providing efficient mass transfer of nutrients and insulin between the islet chamber and the blood stream in the vascularizing chamber, the fibrous or foam matrix having a porosity of about 40 to 95 percent and interconnecting passageways that are equivalent to an open-celled foam having an average pore size of about 10 to 200 microns, the fibers and foam being of an organic or inorganic material, the organic material composed principally of carbon, oxygen, and hydrogen atoms and optionally, nitrogen and sulfur atoms, the inorganic materials being composed of one or more of carbon, titanium, silica, sodium, calcium, strontium, magnesium, zinc and boron atoms.

The present invention also provides a method of presenting insulin-secreting islets of Langerhans to the vascular system of a mammal, the method comprising:

A. providing a bioartificial pancreas as defined above;
B. making the thickness of the pancreas about 1 to 10 millimeters; and
C. implanting the pancreas in a mammal such as in the peritoneal cavity which presents the insulin directly to the liver which is known to be more effective.

DETAILS OF THE INVENTION

Figure 1:
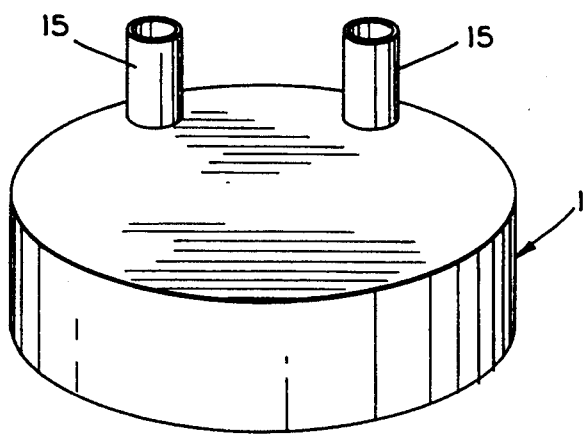
FIG. 1 is a perspective view of an implantable bioartificial pancreas.
Figure 3:
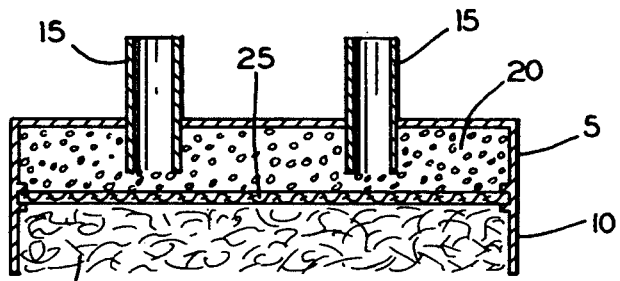
FIG. 3 is a sectional view of the bioartificial pancreas of FIG. 1.

As seen in the drawings, FIG. 1 and 3, a bioartificial pancreas device 1 comprises an islet-containing upper chamber 5, an open on one end vascularizing lower chamber 10, and inlet and outlet means 15 for supplying islets of Langerhans 20 to the islet containing chamber.

A semi-permeable membrane 25 is provided between the islet and vascularizing chambers. The membrane 25 allows passage of nutrients and small vital molecules including oxygen, glucose and insulin but does not allow passage of agents of the immune system such as white cells and antibodies.

Figure 2:
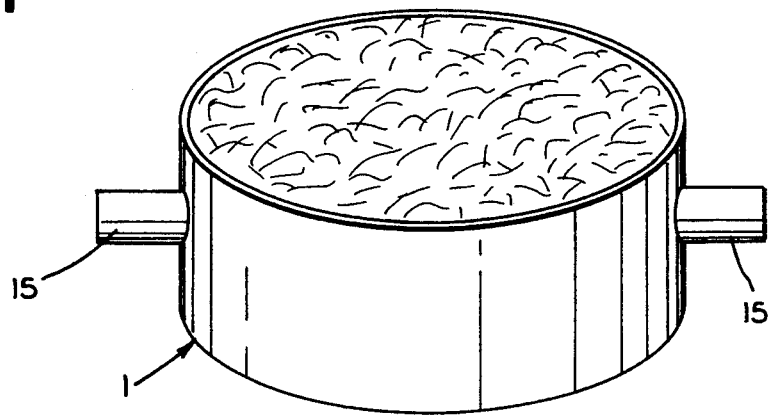
FIG. 2 is a perspective view of another implantable pancreas having dual matrix layers.
Figure 4:
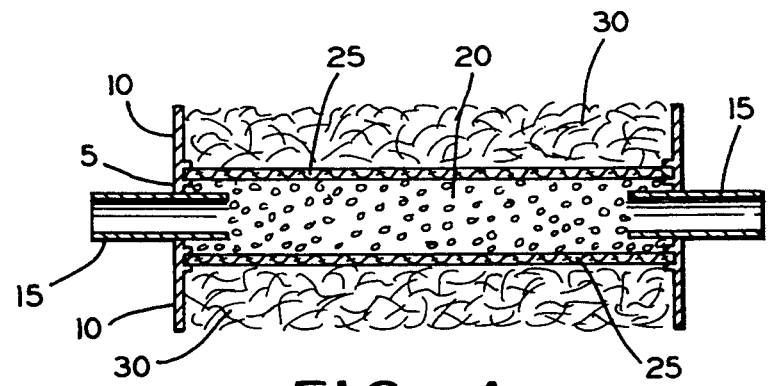
FIG. 4 is a sectional view of the pancreas of FIG. 2.

In the embodiment shown in FIGS. 2 and 4, the pancreas device is shown with dual matrix 30 layers, each of the matrix 30 materials being separated from the islets by a membrane 25.

A biocompatible fibrous or foam matrix 30 is provided in the vascularizing chamber, the matrix 30 being growth factor soaked to promote growth of the vascular system including growth of small capillaries.

The matrix 30 generally has a porosity of as low as about 40 to 50 percent and as high as about 90 to 95% percent. The matrix porosity is preferably about 80 to 90 percent. The matrix foam is an open-celled structure and generally has an average pore size of about 10 to 200 microns, the preferred size being about 50 to 100 microns.

Although the islets of Langerhans cells are highly preferred, other cellular transplants can be used that require immunoprotection and that secrete or metabolize a substance that can permeate the membrane 25. The secreted substances may, for example, be from liver, parathyroid, thyroid, pituitary, neural, adrenal, ovarian or genetically engineered cells. Other useful cells may perform detoxifying functions by removing and metabolizing toxic substances found in the bloodstream.

The fibrous matrix has interconnected openings equivalent in porosity and size openings that are approximately equivalent to the size openings to the foam matrix just described. Hence, the fiber openings are equivalent to the 10 to 200 microns set forth for the foam. The fibers are generally about 10 to 60 or 100 microns in diameter, the preferred average diameter being about 10 to 30 microns.

The total thickness of the matrix is about 1 to 4 mm, the preferred thickness being about 2 to 3 mm. The matrix thickness, thus, is sufficient to absorb proteins, ECM materials, growth factor materials, develop a blood supply, and the matrix also is preferably non-absorbable by the body of the mammal and minimizes fibrotic overgrowth and encapsulation.

Suitable matrix materials are keratin (silk, wool, hair), collagen, of various types, polyolefins such as polyethylene, polypropylene and polybutylene, polyesters such as polyethylene terephthalate and polyethylene adipate, polyurethanes such as polyesterurethanes and polyetherurethanes, glass including glass fibers, stainless steel, silicones, organopolysiloxanes and graphite and combinations thereof. The keratin matrix is keratin, keratin-containing or keratin-like.

The pore size of the highly preferred matrix is at least about 10 microns and optimally 50 to 100 or 120 microns.

For some applications, suitable matrix materials are polyamides including nylon such as polycaprolactam and polyhexamethylene adipate, polyamide-imides, polycarbonates, polyacrylates including polymethyl methacrylate and polyethylmethacrylate and polystyrene.

A suitable fiber and foam matrix is organic or inorganic, the organic material being composed principally of carbon, oxygen, and hydrogen atoms, and optionally nitrogen and/or sulfur atoms. Organic material such as polyolefins, composed of carbon and oxygen atoms are highly useful, such hydrocarbon polymers being non-halogenated and non-fluorinated.

Excellent results have been obtained when the matrix is made of hair in which the average diameter of the hair fiber is about 10 to 15 microns, the fiber length is about ½ to 2 inches, the matrix thickness is about 2 to 3 millimeters and the porosity is about 80 to 85 percent.

In operation after implantation in the peritoneal cavity, or other suitable site, and after a sufficient period of time for device vascularization, usually about four weeks, the islets of Langerhans are delivered to the device islet chamber via the inlet and outlet catheters and ports. The islets take up residence within the islet chamber of the device and are provided with essential nutrients and oxygen via mass transfer from across the immunoprotective membrane from the vascularized chamber of the device. For example, as blood glucose levels rise following a meal, the glucose levels rise rapidly within the vascularized region of the device and glucose diffuses across the immunoprotective membrane resulting in an increase in glucose levels within the islet chamber resulting in the release of insulin from the islets which diffuses back across the immunoprotective membrane being rapidly taken up by the extensive capillary network existing in the vascularized chamber and the insulin is then distributed throughout the body where its ultimate action is to regulate blood glucose levels. The level of glucose control achieved and the number of islets required can be defined using the methods outlined in "A Comparison of Islet Transplantation and Subcutaneous Insulin Injections for the Treatment of Diabetes", *Computers in Biology and Medicine*, Volume 21, pp. 417–427, 1991, Brian Smith, Jeffrey G. Sarver, Ronald L. Fournier.

In another embodiment of the invention, baffle means are provided inside the first chamber for assisting in even distribution of the metabolically active cells such as islets of Langerhans therein.

Figure 5A:
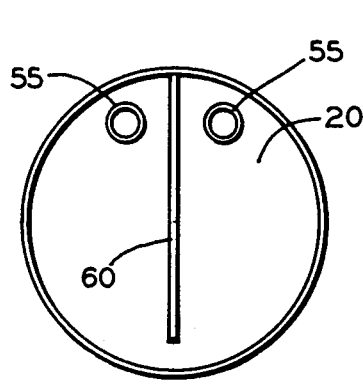
FIG. 5a is a top plan view of the first chamber showing baffle means for assisting in even distribution of biologically active cells such as islets of Langerhans.

As shown in FIG. 5a, a first chamber 50 is provided that is similar to the first chamber 20 of FIG. 3. An inlet and outlet tube means 55 are provided for the entry and exit of the islets. In FIG. 5, baffle means is provided comprising a plate 60 that assists in the even distribution of the islets in the chamber after supplying the islets. As in FIGS. 1–4 the islets form a layer next to a porous membrane.

The plate 60 is generally perpendicular to the bottom of the first chamber and the longitudinal axis of the plate 60 extends generally along a diameter of the chamber.

Figure 5B:
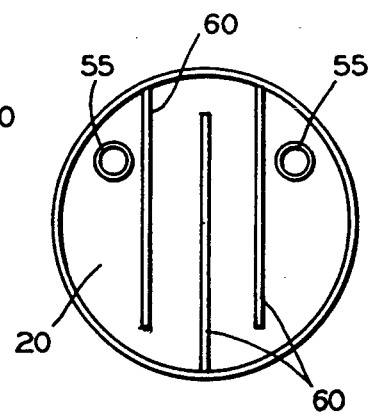
FIG. 5b is another embodiment showing baffle means in the first chamber.
Figure 5C:
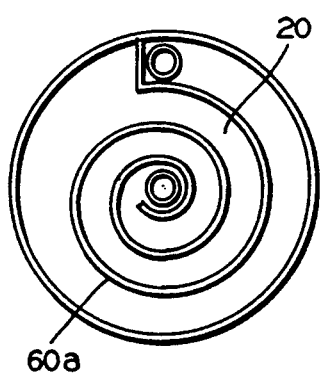
FIG. 5c is still another embodiment showing baffle means in the first chamber.

As shown in FIG. 5b, the baffle means comprises a plurality of plates, preferably 3, spaced about equally distance apart and parallel to each other. In FIG. 5c, the baffle in the plan view is a generally helically coiled or sprial-shaped member 60a.

Figure 6:
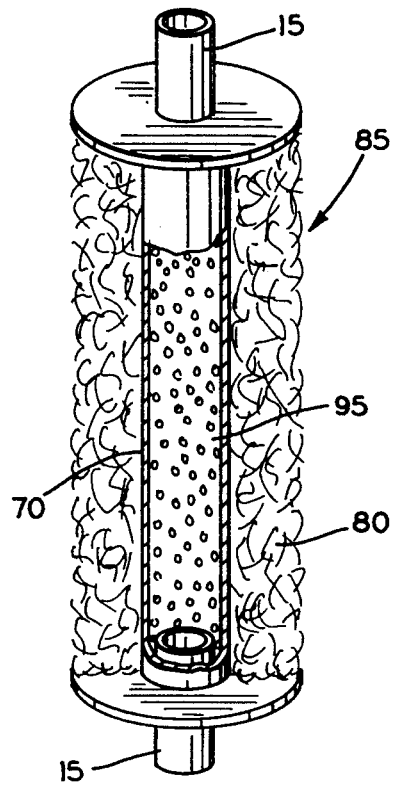
FIG. 6 is a perspective view of a first chamber for islets and other active cells, the chamber being in the form of an elongated tube or hollow fiber.

In FIG. 6, a hollow fiber/matrix assembly 85 is shown in which a hollow fiber 70 serves as the first chamber, the fiber being surrounded by a matrix 80 which is similar to matrix 30 shown in FIGS. 3–4.

Figure 6A:
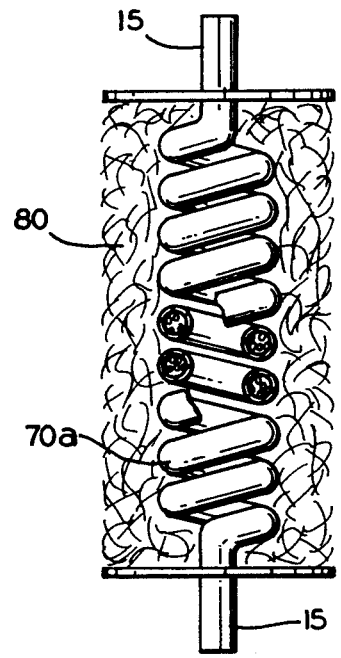
FIG. 6a is a side elevational view of another embodiment showing the first chamber in the form of a helically shaped hollow fiber.

In FIG. 6a, the first chamber is an elongated helically coil-shaped or spiral-shaped hollow fiber 70a embedded in the matrix 80.

Figure 7:
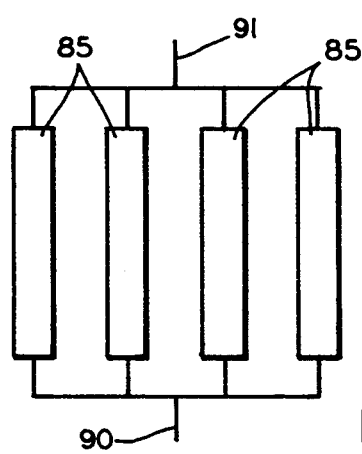
FIG. 7 is a top plan schematic view of a plurality of first chamber hollow fibers, the follow fibers being a common inlet and a common outlet.

FIG. 7 shows a plan view of four hollow fiber 70/matrix 80 first chamber assemblies. The first chambers 85 are connected together with a common inlet 90 and a common outlet 91.

In the embodiments shown in FIGS. 5a, 5b, 5c, 6, 6a and 7, the active cells such as the islets form a layer next to a semi-permeable membrane 95 such as the membrane 25 in FIGS. 3 and 4. The baffle means provides an even distribution of the active cells as they are introduced into the first chamber and used therein.

Thus, the present invention provides an effective and highly useful bioartificial organ for implantation into an animal comprising a housing having a first enclosed chamber containing metabolically active cells, at least one vascularizing chamber having an opening on one end thereof that provides access to surrounding tissue, inlet means for supplying cells to the first chamber, outlet means for removing cells from the first chamber, and a semi-permeable membrane separating and in communication with the first chamber and vascularizing chamber, the membrane providing immunoprotection of the active cells from the vascular area within the vascularizing chamber and around the implanted device, the membrane allowing passage of small molecules including nutrients and waste products between the first and vascularizing chambers and not allowing passage of agents of an immune system to the first chamber, and a biocompatible fibrous or porous foam matrix in the vascularizing chamber to provide a neovascular formation region for enhancing growth of small capillaries for providing efficient mass transfer of substances between first chamber and the capillaries in the vascularizing chamber, the fibrous or foam matrix having a porosity of about 40 to 95 percent and interconnecting passageways of about 10 to 120 microns, the fibers and foam being of an organic or inorganic material, the organic material composed principally of carbon, oxygen, and hydrogen atoms and optionally, nitrogen and sulfur atoms, the inorganic materials being composed of one or more of carbon, titanium, silica, sodium, calcium, strontium, magnesium, zinc and boron atoms, there being baffle means in the first enclosed chamber for assisting in even distribution of the metabolically active cells.

What is claimed is:

1. A bioartificial organ for implantation into an animal comprising a housing having a first enclosed chamber containing metabolically active cells, at least one vascularizing chamber having an opening on one end thereof that provides access to surrounding tissue, inlet means for supplying cells to the first chamber, outlet means for removing cells from the first chamber, and a semi-permeable membrane separating and in communication with the first chamber and vascularizing chamber, the membrane providing immunoprotection of the active cells from the vascular area within the vascularizing chamber and around the implanted device, the membrane allowing passage of small molecules including nutrients and waste products between the first and vascularizing chambers and not allowing passage of agents of an immune system to the first chamber, and a biocompatible fibrous or porous foam matrix having fibers or foam in the vascularizing chamber to provide a neovascular formation region for enhancing growth of small capillaries for providing efficient mass transfer of substances between first chamber and the capillaries in the vascularizing chamber, the fibrous or foam matrix having a porosity of about 40 to 95 percent and interconnecting passageways of about 10 to 120 microns, the fibers and foam being of an organic material or inorganic material, the organic material composed principally of carbon, oxygen, and hydrogen atoms, or sulfur atoms, oxygen atoms and hydrogen atoms, or carbon atoms, oxygen atoms, hydrogen atoms and nitrogen atoms, the inorganic materials being composed of at least one of carbon, titanium, silica, sodium, calcium, strontium, magnesium, zinc and boron atoms, there being baffle means in the first enclosed chamber for assisting in even distribution of the metabolically active cells.

2. A bioartificial organ as defined in claim 1 in which the baffle means is a baffle plate in the first chamber.

3. A bioartificial organ as defined in claim 1 in which the baffle means is three baffle plates generally parallel to each other to provide even distribution of the cells in the first chamber.

4. An organ as defined in claim 3 in which there are three baffle plates.

5. A bioartificial organ as defined in claim 1 in which the baffle means is spiral-shaped coil forming a labyrinth inside the first chamber to assist in even distribution of the cells.

6. A bioartificial implantable pancreas comprising a housing having a first enclosed chamber containing islets of Langerhans, at least one vascularizing chamber having an opening on one end thereof that provides access to surrounding tissue, a plurality of insulin-secreting islets of Langerhans in the first chamber, inlet means for supplying islets to the first chamber, outlet means for removing islets from the first chamber, a semi-permeable membrane between the first islet chamber and vascularizing chamber, the membrane providing immunoprotection of the islets from the vascular area within the vascularizing chamber and around the implanted device, the membrane allowing passage of small molecules including oxygen and insulin between the first and vascularizing chambers and not allowing passage of agents of the immune system to the first chamber, and a biocompatible fibrous or porous foam matrix having fibers or foam in the vascularizing chamber to provide a neovascular formation region for enhancing the growth of small capillaries for providing efficient mass transfer of nutrients, glucose, oxygen, and insulin between in the islet chamber and the blood stream in the vascularizing chamber, the fibrous or foam matrix having a porosity of about 40 to 95 percent and interconnecting passageways having an average pore size of about 10 to 200 microns, the fibers and foam being of an organic or inorganic material, the organic material composed principally of carbon, oxygen, and hydrogen atoms and optionally, nitrogen and sulfur atoms, the inorganic materials being composed of at least one of carbon, titanium, silica, sodium, calcium, strontium, magnesium, zinc and boron atoms, and there being baffle means inside the first chamber to assist in providing an even distribution of the islet cells in the first chamber.

7. A bioartificial organ for implantation into an animal comprising a housing having a first enclosed chamber containing metabolically active cells, at least one vascularizing chamber having an opening on one end thereof that provides access to surrounding tissue, inlet means for supplying cells to the first chamber, outlet means for removing cells from the first chamber, and a semi-permeable membrane separating and in communication with the first chamber and vascularizing chamber, the membrane providing immunoprotection of the active cells from the vascular area within the vascularizing chamber and around the implanted device, the membrane allowing passage of small molecules including nutrients and waste products between the first and vascularizing chambers and not allowing passage of agents of an immune system to the first chamber, and a biocompatible fibrous or porous foam matrix having fibers and foam in the vascularizing chamber to provide a neovascular formation region for enhancing growth of small capillaries for providing efficient mass transfer of substances between first chamber and the capillaries in the vascularizing chamber, the fibrous or foam matrix having a porosity of about 40 to 95 percent and interconnecting passageways of about 10 to 120 microns, the fibers and foam being of an organic or inorganic material, the organic material composed principally of carbon, oxygen, and hydrogen atoms and optionally, nitrogen and sulfur atoms, the inorganic materials being composed of at least one of carbon, titanium, silica, sodium, calcium, strontium, magnesium, zinc and boron atoms, the first active cell containing chamber being a longitudinally extending hollow fiber.

8. An organ as defined in claim 7 in which cell containing chamber is coiled helically-shaped hollow fiber.

9. An organ as defined in claim 7 in which there are a plurality of parallel hollow fibers, each inlet means and outlet means of the fibers being connected to a common feed source and a common exit source.

* * * * *